United States Patent [19]

Rodan et al.

[11] Patent Number: 5,780,291
[45] Date of Patent: Jul. 14, 1998

[54] WNT-X GROWTH FACTOR POLYPEPTIDE, DNA ENCODING SAME, AND WNT-X ANTIBODY

[75] Inventors: Gideon A. Rodan, Bryn Mawr; Su Jane Rutledge, East Greenville; Azriel Schmidt, Bryn Mawr, all of Pa.

[73] Assignee: Merck & Co., Inc., Rahway, N.J.

[21] Appl. No.: 647,928

[22] PCT Filed: Dec. 19, 1994

[86] PCT No.: PCT/US94/14708

§ 371 Date: May 22, 1996

§ 102(e) Date: May 22, 1996

[87] PCT Pub. No.: WO95/17416

PCT Pub. Date: Jun. 29, 1995

Related U.S. Application Data

[63] Continuation of Ser. No. 172,365, Dec. 22, 1993, abandoned.

[51] Int. Cl.$^6$ ............ C07K 14/475; C12N 1/21; C12N 5/10; C12N 15/12

[52] U.S. Cl. ............ 435/252.3; 435/320.1; 435/325; 435/172.3; 530/350; 530/399; 530/387.9; 536/23.5

[58] Field of Search ............ 530/350, 399, 530/387.9; 435/7.1, 69.1, 69.4, 172.3, 252.3, 320.1, 325; 536/23.5

[56] References Cited

PUBLICATIONS

Bowie et al. Science 247:1306–1310, 1990.

Nusse and Varmus, "Wnt Genes", Cell, vol. 69, pp. 1073–1087 (1992).

Wainwright, et al., "Isolation of a human gene with protein sequence similarity to human and murine int–1 . . . ", The EMBO Journal, vol. 7, No. 6, pp. 1743–1748 (1988).

van 't Veer, et al., "Molecular Cloning and Chromosomal Assignment of the Human Homolog of int–1 . . . ", Mol andCell Biology, vol. 4, No. 11, pp. 2532–2534 (1984).

Gavin, et al., "Expression of multiple novel Wnt–1/int–1 related genes during fetal and adult mouse development", Genes & Development, vol. 4, pp. 2532–2534 (1984).

Nusse and Varmus, "Manu Tumors Induced by the Mouse Mammary Tumor Virus Contain a Provirus Integrated . . . ", Cell, vol. 31, pp. 99–109 (1982).

Rijsewink, et al., "Transfection of the int–1 mannary in cuboidal RAC mammary cell line results in morphological . . . ", The EMBO Journal, vol. 6, No. 1, pp. 127–131 (1987).

Brown, et al., "A Retrovirus Vector Expressing the Putative Mammary Oncogene int–1 Causes Partial . . . ", Cell, vol. 46, pp. 1001–1009 (1986).

Savard, "Body Axis Determination During Early Development in Amphibians", Biochem. Cell. Biol., vol. 70, pp. 875–891, (1992).

McMahon, et al., Nucleotide sequence, chromosomal localization and decelopmental expression of the mouse int–1–related gene, Development, vol. 107, pp. 643–650 (1989).

Lin, et al., "Role of Endocrine, Autocrine, and Paracrine Interactions in the Development of Mammary . . . ", Cancer Research, vol. 52, pp. 4413–4419, (1992).

Barton, et al., "Bacillus thuringiensis –Endotoxin Expressed in Transgenic Vicotiana tabacum Provides Resistance . . . ", Plant Physiol., vol. 85, pp. 355–359, (1987).

Gelvin, et al., "Biotechnology News and Views", Plant Mol. Biol., vol. 8, pp. 355–359 (1987).

Primary Examiner—Elizabeth C. Kemmerer
Attorney, Agent, or Firm—Michael D. Yablonsky; Jack L. Tribble

[57] ABSTRACT

A novel member of the Wnt-family of growth factors, termed Wnt-x, has been identified and DNA encoding the growth factor has been isolated, purified, sequenced and expressed in host cells. This DNA encoding the novel Wnt-x protein and host cells expressing the Wnt-x protein are used to identify modulators of the Wnt-x growth factor.

6 Claims, 4 Drawing Sheets

```
         10                        30                         50
gaattccggggcacc ttccgggctgcgcgggga gtcttcgggagctgctgagac
                                                      M  L  R  P 70                        90                        110
cgggtggtgcggagga agctgcgcagctgccccc gcgccagccgcccgtcctg
G  G  A  E  E  A  A  Q  L  P  L  R  R  R  A  S  A  P  V  P  V 130                       150                        170
tgccgtcgccgcccga cggccccccgacgtccc cggcttcggccgcctagttcttgctgcc
P  S  P  A  A  P  D  G  S  R  A  S  A  R  L  G  L  A  C  L 190                       210                        230
ttctgctcctgctgct gctgacgttgctgcgcc gccgtagacacgtcctggtggtacattg
L  L  L  L  L  T  L  L  L  T  L  P  A  R  V  D  T  S  W  W  Y  I  G 250                       270                        290
gggcactggggcacga cgagtgatctgtgacaat atccctgtttggttgtgagcgggcagcggc
A  L  G  A  R  V  I  C  D  N  I  P  G  L  V  S  R  Q  R  Q 310                       330                        350
agctgccagcgttacc cagacatcatgcgttcag tgggcgagggtgccgagaatgaa
L  C  Q  R  Y  P  D  I  M  R  S  V  G  E  G  A  R  E  W  I 370                       390                        410
tccgagagtgtcagca ccaattccgccaccaccc gctggaactgtaccaccctggaccggg
R  E  C  Q  H  Q  F  R  H  H  R  W  N  C  T  T  L  D  R  D
```

FIG. 1A

```
                430                      450                      470
accacaccgtctttggccgtgtcatgctcagaagtagccgagacggagcttttgtatg
 H  T  V  F  G  R  V  M  L  R  S  S  R  D  G  A  F  V  Y  A
                490                      510                      530
ccatctcatcagcaggggtagtccacgctattactcgcctgtagcaggggtgaactga
 I  S  S  A  G  V  V  H  A  I  T  R  A  C  S  Q  G  E  L  S
                550                      570                      590
gtgtgtgcagctgtgaccccctacacccgtgccgacacaccatgaccagcgtggggactttg
 V  C  S  C  D  P  Y  T  R  G  R  H  H  D  Q  R  G  D  F  D
                610                      630                      650
actggggtggctgcagtgacaacatccactacggtgtccgttttgccaaggccttcgtgg
 W  G  G  C  S  D  N  I  H  Y  G  V  R  F  A  K  A  F  V  D
                670                      690                      710
atgccaaggagaggagaggcttaaggatgcccgggccctcatgaacttacataataaccgct
 A  K  E  K  R  L  K  D  A  R  A  L  M  N  L  H  N  N  R  C
                730                      750                      770
gtggtcgcacggtcagtactcatgtctgtgtgcggggtttctgaagctggagtgta
 G  R  T  V  S  T  H  V  C  A  V  R  R  F  L  K  L  E  C  K
```

```
790                    810                       830
agtgccatggcgtgagtggttcctgcacctgctgcgtgcactctcagatt
 C  H  G  V  S  G  S  C  T  L  R  T  C  W  R  A  L  S  D  F 850                       870                       890
tccgccgcacaggtgattacctgcgcggacgctatgatgggctgcaggtgatggcca
 R  R  T  G  D  Y  L  R  R  R  Y  D  G  A  V  Q  V  M  A  T 910                       930                       950
cccaagatggtgccaacttcaccgcgcagcccgccaaggctatcgccgtgccacccgactg
 Q  D  G  A  N  F  T  A  A  R  Q  G  Y  R  R  A  T  R  T  D 970                       990
atcttgtctacttgacaaccgctccagattactgtgtcttggacaaggctgcaggttccc
 L  V  Y  L  T  T  A  P  D  Y  C  V  L  D  K  A  A  G  S  L 1030                      1050                      1070
taggcactgcgcaggccgtgtctgcagacatcaaaggaacagacggtgtgaaatca
 G  T  A  G  R  V  C  S  K  T  S  K  G  T  D  G  C  E  I  M 1090                      1110                      1130
TGTGCTGTGTGGCCGAGGGTACGACACAACTGAGTCACCCGTGTTACCCAGTGTGAGTGCA
 C  C  G  R  G  Y  D  T  T  R  V  T  R  V  T  Q  C  E  C  K
```

```
                              1170                                1190
           1150     AAITCCACTGGTGCTGTGCTGTACGGTGCAAGGAATGCAGAAATACTGTGGACGTCCATA
AATTCCACTGGTGCTGTGCTGTACGGTGCAAGGAATGCAGAAATACTGTGGACGTCCATA
 F  H  W  C  C  A  V  R  C  K  E  C  R  N  T  V  D  V  H  T 1210                   1230                 1250
CTTGCAAAGCCCCCAAGAAGGCAGAGTGGCTGGACCAGACCTGAACACAGATACCTCA
 C  K  A  P  K  K  A  E  W  L  D  Q  T  *

1270
CTCATCCCTCCC
```

WNT-X GROWTH FACTOR POLYPEPTIDE, DNA ENCODING SAME, AND WNT-X ANTIBODY

This is a 35 U.S.C. §371 filing of PCT/US94/14708, filed Dec. 19, 1994, and a continuation of U.S. Ser. No. 08/172,365, filed Dec. 22, 1993, now abandoned.

BACKGROUND OF THE INVENTION

The Wnt growth factor family is composed of several structurally related proteins. The Wnt-1 proto-oncogene (int-1) was originally identified from mammary tumors induced by mouse mammary tumor virus (MMTV) due to an insertion of viral DNA sequence (Nusse and Varmus, 1982, Cell, 31, pp. 99–109). At least ten Wnt genes were identified in the mouse (Wnt-1, 2, 3, 3a, 4, 5a, 5b, 6, 7a, and 7b) [Gavin et al., (1990), Genes Dev., 4, pp. 2319–2332] and seven Wnt genes have been identified in the human (Wnt-1, 2, 3, 4, 5a, 7a, and 7b) by cDNA cloning (Vant Veer et al., 1984, Mol. Cell. Biol., 4, pp. 2532–2534; Wainright et al., 1988, EMBO J., 7, pp. 1743–1748). In situ hybridization studies have shown that the expression of many Wnt growth factor genes were specifically related to patterning and morphogenesis during early neural development in the central nervous system, suggesting that the expression of these genes are required for patterning and development in the Drosophila and invertebrates. In adult mice, the expression level of Wnt-1 mRNA is detected only in the testis during later stages of sperm development. Wnt-1 protein is about 42 KDa and contains an amino terminal hydrophobic region, which may function as a signal sequence for secretion (Nusse and Varmus, supra). The expression of Wnt-2/irp is detected in mouse fetal and adult tissues and its distribution does not overlap with the expression pattern for Wnt-1. Wnt-3 is associated with mouse mammary tumorigenesis. The expression of Wnt-3 in mouse embryos detected in the neural tubes and in the limb buds. Wnt-5a transcripts are detected in the developing fore- and hind limbs at 9.5 through 14.5 days and highest levels are concentrated in apical ectoderm at the distal tip of limbs (Nusse and Varmus, 1992, Cell, 69, pp. 1073–1087).

SUMMARY OF THE INVENTION

A new member of the Wnt growth factor family from humans is disclosed. DNA encoding the new Wnt growth factor, termed Wnt-x, is also disclosed as is the detection of Wnt-x expression in bone tissues and in bone-derived cells. Also disclosed is the role of Wnt-x in the maintenance of mature osteoblasts and the use of the Wnt-x growth factor as a therapeutic agent or in the development of other therapeutic agents to treat bone-related diseases.

BRIEF DESCRIPTION OF THE DRAWINGS

FIGS. 1A–1D—Nucleotide sequence of Wnt-x cDNA (SEQ ID NO:7) with the amino acid sequence of Wnt-x (SEQ ID NO:8) deduced from the cDNA sequence is shown.

DETAILED DESCRIPTION OF THE INVENTION

The present invention relates to cDNA encoding a novel growth factor termed Wnt-x. The present invention is also related to recombinant host cells which express the cloned Wnt-x-encoding DNA contained in a recombinant expression plasmid. The present invention is also related to a method for the screening of substances which modulate Wnt-x protein activity. The DNA of the present invention is isolated from Wnt-x producing cells. Wnt-x, as used herein, refers to a growth factor which is specifically expressed in bone cells. The present invention also relates to a unique growth factor protein, also described as Wnt-x, which is isolated from Wnt-x producing cells. Wnt-x protein, as used herein, refers to a growth factor protein which is specifically produced by bone cells.

Mammalian cells capable of producing Wnt-x include, but are not limited to, cells derived from tissues including heart, brain and bone. Transformed mammalian cell lines which produce Wnt-x include, but are not limited to, giant cell tumor cells. The preferred cells for the present invention include human giant cell tumor cells.

Other cells and cell lines may also be suitable for use to isolate Wnt-x cDNA. Selection of suitable cells may be done by screening for Wnt-x produced by the cells. Methods for detecting Wnt growth factor RNA and activity are well known in the art [Nusse, R. and Varmus, H., 1992, Cell, 69, pp. 1073–1978] and measure the level of Wnt-x RNA produced by the cells. Cells which possess Wnt-x activity in this assay may be suitable for the isolation of Wnt-x cDNA.

Cells which are responsive to Wnt gene activity are known in the art, and include but are not limited to, the mouse mammary epithelial cell lines C57MG [Brown et al. (1986), Cell, 46, pp. 3971–3977] and RAC cell lines [Rijsewijk et al. (1987), EMBO J., 6, pp. 127–131], and the rat pheochromocytoma cell line PC12 (ATCC CRL 1721). These cells display an altered morphology and enhanced growth properties upon the introduction and expression of Wnt genes and are suitable for use in an assay procedure for the identification of Wnt-x modulators, or as cells responsive to added recombinantly produced Wnt-x protein.

Any of a variety of procedures may be used to clone Wnt-x cDNA. These methods include, but are not limited to, direct functional expression of the Wnt-x cDNA following the construction of an Wnt-x-containing cDNA library in an appropriate expression vector system. Another method is to screen an Wnt-x-containing cDNA library constructed in a bacteriophage or plasmid shuttle vector with a labelled oligonucleotide probe designed from the amino acid sequence of the Wnt-x protein. The preferred method consists of screening an Wnt-x-containing cDNA library constructed in a bacteriophage or plasmid shuttle vector with a partial cDNA encoding the Wnt-x protein. This partial cDNA is obtained by the specific PCR amplification of Wnt-x DNA fragments through the design of degenerate oligonucleotide primers from the amino acid sequence known for other Wnt-x-family growth factors which are related to the Wnt-x protein.

It is readily apparent to those skilled in the art that other types of libraries, as well as libraries constructed from other cells or cell types, may be useful for isolating Wnt-x-encoding DNA. Other types of libraries include, but are not limited to, cDNA libraries derived from other cells or cell lines other than human giant tumor cells, and genomic DNA libraries.

It is readily apparent to those skilled in the art that suitable cDNA libraries may be prepared from cells or cell lines which have Wnt-x activity. The selection of cells or cell lines for use in preparing a cDNA library to isolate Wnt-x cDNA may be done by first measuring cell associated Wnt-x activity using the known assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding Wnt-x may also be isolated from a suitable genomic DNA library.

Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone the Wnt-x gene by one of the preferred methods, the amino acid sequence or DNA sequence of Wnt-x or a homologous protein is necessary. To accomplish this, Wnt-x protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial Wnt-x DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the Wnt-x sequence but others in the set will be capable of hybridizing to Wnt-x DNA even in the presence of DNA oligonucleotides with mismatches. The mismatched DNA oligonucleotides may still sufficiently hybridize to the Wnt-x DNA to permit identification and isolation of Wnt-x encoding DNA.

Using one of the preferred methods, cDNA clones encoding Wnt-x are isolated in a two-stage approach employing polymerase chain reaction (PCR) based technology and cDNA library screening. In the first stage, $NH_2$-terminal and internal amino acid sequence information from the purified Wnt-x or a homologous protein is used to design degenerate oligonucleotide primers for the amplification of Wnt-x-specific DNA fragments. In the second stage, these fragments are cloned to serve as probes for the isolation of full length cDNA from a cDNA library derived from human giant cell tumor cells.

The sequence for the near full-length cDNA encoding Wnt-x is shown in Table 1, and was designated clone Wnt-x. The deduced amino acid sequence of Wnt-x from the cloned cDNA is shown in Table 2. Inspection of the determined cDNA sequence reveals the presence of a single, large open reading frame that approximately encodes for a 397 amino acid protein.

The cloned Wnt-x cDNA obtained through the methods described above may be recombinantly expressed by molecular cloning into an expression vector containing a suitable promoter and other appropriate transcription regulatory elements, and transferred into prokaryotic or eukaryotic host cells to produce recombinant Wnt-x. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant Wnt-x in mammalian cells. Commercially available mammalian expression vectors which may be suitable for recombinant Wnt-x expression, include but are not limited to, pMClneo (Stratagene), pXT1 (Stratagene), pSG5 (Stratagene), pcDNAI, pcDNAIamp (Invitrogen), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565) expression vector for expression in a host cell. Host cells may be prokaryotic or eukaryotic, including but not limited to bacteria, DNA encoding Wnt-x may also be cloned into an yeast, mammalian cells including but not limited to cell lines of human, bovine, porcine, monkey and rodent origin, and insect cells including but not limited to drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

The expression vector may be introduced into host cells via any one of a number of techniques including but not limited to transformation, transfection, protoplast fusion, and electroporation. The expression vector-containing cells are individually analyzed to determine whether they produce Wnt-x protein. Identification of Wnt-x expressing cells may be done by several means, including but not limited to immunological reactivity with anti-Wnt-x antibodies, and the presence of host cell-associated Wnt-x activity.

Expression of Wnt-x DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the Wnt-x cDNA sequence(s) that yields optimal levels of Wnt-x protein, Wnt-x cDNA molecules including but not limited to the following can be constructed: the full-length open reading frame of the Wnt-x cDNA and various constructs containing portions of the cDNA encoding only specific domains of the protein or rearranged domains of the protein. All constructs can be designed to contain none, all or portions of the 5' and/or 3' untranslated region of Wnt-x cDNA. Wnt-x activity and levels of protein expression can be determined following the introduction, both singly and in combination, of these constructs into appropriate host cells. Following determination of the Wnt-x cDNA cassette yielding optimal expression in transient assays, this Wnt-x cDNA construct is transferred to a variety of expression vectors (including recombinant viruses), including but not limited to those for mammalian cells, plant cells, insect cells, oocytes, bacteria, and yeast cells.

Levels of Wnt-x protein in host cells is quantitated by a variety of techniques including, but not limited to, immunoaffinity and/or ligand affinity techniques. Wnt-x-specific affinity beads or Wnt-x-specific antibodies are used to isolate $^{35}$S-methionine labelled or unlabelled Wnt-x protein. Labelled Wnt-x protein is analyzed by SDS-PAGE. Unlabelled Wnt-x protein is detected by Western blotting, ELISA or RIA assays employing Wnt-x specific antibodies.

Following expression of Wnt-x in a host cell, Wnt-x protein may be recovered to provide Wnt-x in active form. Several Wnt-x purification procedures are available and suitable for use. Recombinant Wnt-x may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant Wnt-x can be separated from other cellular proteins by use of an immuno-affinity column made with monoclonal or polyclonal antibodies specific for full length Wnt-x, or polypeptide fragments of Wnt-x.

Monospecific antibodies to Wnt-x are purified from mammalian antisera containing antibodies reactive against Wnt-x or are prepared as monoclonal antibodies reactive with Wnt-x using the technique of Kohler and Milstein, Nature 256: 495–497 (1975). Monospecific antibody as used herein is defined as a single antibody species or multiple antibody species with homogenous binding characteristics for Wnt-x. Homogenous binding as used herein refers to the ability of the antibody species to bind to a specific antigen or epitope, such as those associated with the Wnt-x, as described above. Wnt-x specific antibodies are raised by immunizing animals such as mice, rats, guinea pigs, rabbits, goats, horses and the like, with an appropriate concentration of Wnt-x either with or without an immune adjuvant.

Preimmune serum is collected prior to the first immunization. Each animal receives between about 0.1 µg and about 1000 µg of Wnt-x associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the Wnt-x protein in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of Wnt-x in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with Wnt-x are prepared by immunizing inbred mice, preferably Balb/c, with Wnt-x. The mice are immunized by the IP or SC route with about 1 µg to about 100 µg, preferably about 10 µg, of Wnt-x in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 µg of Wnt-x in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes, with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells on about days 14, 18, and 21 and are screened for antibody production by an immunoassay such as solid phase immunoradioassay (SPIRA) using Wnt-x as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-Wnt-x mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of Wnt-x in body fluids or tissue and cell extracts.

It is readily apparent to those skilled in the art that the above described methods for producing monospecific antibodies may be utilized to produce antibodies specific for Wnt-x polypeptide fragments, or full-length Wnt-x polypeptide.

Wnt-x antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing Wnt-x or Wnt-x fragments are slowly passed through the column. The column is then washed with phosphate buffered saline until the optical density ($A_{280}$) falls to background, then the protein is eluted with 0.23M glycine-HCl (pH 2.6). The purified Wnt-x protein is then dialyzed against phosphate buffered saline.

The novel Wnt-x growth factor of the present invention is suitable for use in an assay procedure for the identification of compounds which modulate the Wnt-x activity. Modulating Wnt-x activity, as described herein includes the inhibition or activation of the protein and also includes directly or indirectly affecting the normal regulation of the Wnt-x activity. Compounds which modulate the Wnt-x activity include agonists, antagonists and compounds which directly or indirectly affect regulation of the Wnt-x activity.

The Wnt-x growth factor of the present invention may be obtained from both native and recombinant sources for use in an assay procedure to identify Wnt-x modulators. In general, an assay procedure to identify Wnt-x modulators will contain the Wnt-protein of the present invention, and a test compound or sample which contains a putative Wnt-x modulator. The test compounds or samples may be tested directly on, for example, purified Wnt-x protein whether native or recombinant, subcellular fractions of Wnt-x-producing cells whether native or recombinant, and/or whole cells expressing the Wnt-x whether native or recombinant. The test compound or sample may be added to the Wnt-x in the presence or absence of a known Wnt-x modulator. The modulating activity of the test compound or sample may be determined by, for example, analyzing the ability of the test compound or sample to bind to Wnt-x protein, activate the protein, inhibit Wnt-x activity, inhibit or enhance the binding of other compounds to the Wnt-x protein, modifying receptor regulation, or modifying an intracellular activity.

The identification of modulators of Wnt-x activity are useful in treating disease states involving the Wnt-x activity. Other compounds may be useful for stimulating or inhibiting activity Wnt-x. Such compounds could be of use in the treatment of diseases in which activation or inactivation of the Wnt-x protein results in either cellular proliferation, cell death, nonproliferation, induction of cellular neoplastic transformations or metastatic tumor growth and hence could be used in the prevention and/or treatment of cancers such as bone and breast cancer for example. The isolation and purification of an Wnt-x-encoding DNA molecule would be useful for establishing the tissue distribution of Wnt-x as well as establishing a process for identifying compounds which modulate Wnt-x activity and/or expression.

Isolated and purified Wnt-x DNA would also be useful for the recombinant production of large quantities of Wnt-x protein. The ability to produce large quantities of the protein would be useful for the production of a therapeutic agent comprising Wnt-x protein. A therapeutic agent comprised of Wnt-x protein would be useful in the treatment of Wnt-x-related diseases or conditions which are Wnt-x responsive.

Sequence analysis of the cloned Wnt-x DNA from a human heart library revealed that the predicted amino acid sequence of Wnt-x contained the consensus amino acid residues which are common to all the members of the Wnt protein family. It was determined that the amino acid sequence of Wnt-x is most similar to Wnt-2 with greater than 60% identity. The similarity to the other members of this family was in the range of 42–55%. By Northern hybridization analysis experiments, high expression levels of Wnt-x mRNA was found in bone tissues, such as tibia of three-week-old normal rat and human giant cell tumor cells. These findings show that the Wnt-x gene is expressed preferentially in bone tissues and its expression plays a role in maintaining the mature osteoblast phenotype.

In addition to the cloning of the novel Wnt-X DNA, the expression of other Wnt-family genes, such as Wnt-3, Wnt-4, Wnt-5a and Wnt-6, were identified in bone cells and tissues by PCR. Hybridization studies with the cloned cDNA fragments from each gene shows detectable expression levels of Wnt-3 mRNA in mouse calvaria cells. Vitamin D3 and PTH treatment of the osteoblastic cells MB 1.7, MB 1.10 (p6), which have potent activity to induce osteoclast-like cells in co-culture with bone marrow cells, increased the expression level of Wnt-3 mRNA. This increase in transcription required more than 2 days exposure to vitamin D3. These observations raise the possibility that the expression of Wnt genes may contribute to the influence of vitamin D3 on osteoblasts.

In contrast to the effect of vitamin D3 on the expression of Wnt-3 mRNA, the expression of Wnt-5a was down regulated by vitamin D3 in mouse calvaria cells. In situ hybridization has shown that both Wnt-3 and Wnt-5a expression was detected in limb buds in fetal development, and the expression of both Wnt-3 and Wnt-5a were regulated by treatment of vitamin D3. However, the regulatory effect of vitamin D3 on expression was opposite in mouse osteoblasts in vitro. This suggests that Wnt growth factors are functioning in opposite ways as shown by treatment with vitamin D3. Vitamin D3 may affect bone development by changing the expression levels of Wnt growth factor genes in several different populations of osteoblastic cells. These findings show that the Wnt gene family, including Wnt-x, is involved in bone development and bone cell differentiation.

Cloning Of Wnt Growth Factor Genes

The polymerase chain reaction (PCR) method was used to identify Wnt growth factor genes. PCR amplification of cDNA prepared from rat calvaria, mouse calvaria cells and human giant cell tumor yielded a set of cDNA fragments of about 390 bp. These PCR products were cloned into plasmid pBS and digested with PvuII, and sequenced. The deduced amino acid residues by the DNA sequences indicated that these PCR products encode five different Wnt factor genes; four of them are identical to known sequence of Wnt-3, 4, 5a, and 6. A novel member of Wnt growth factor gene family was identified from rat calvaria and was designated Wnt-x. Wnt-3 and Wnt-4 were identified from human giant cell tumor cells. Wnt-4 and Wnt-6 were identified from mouse calvaria.

Wnt-x cDNA isolated from rat calvaria is a novel Wnt family gene and sequence analysis exhibited that this 390 bp Wnt-x cDNA fragment is most similar to Wnt-2(irp) with 68% homology in amino acid sequence. The similarity of the other members of this family is the range of 42–55%.

Cloning Of Human Wnt-x

With primers designed according to the rat Wnt-x DNA sequence and mouse consensus sequence, PCR amplification of cDNA prepared from human giant cell tumor was carried out, and yielded a cDNA fragment of about 350 bp encoding the Wnt-x human gene. A cDNA fragment of the PCR product of human Wnt-x sequence was used as a probe to screen the human cDNA libraries. After screening approximately 0.5 million plaques of human heart library (Clontech, Calif.), we obtained only one positive clone of 1000 bp. Sequence analysis revealed that the deduced amino acid sequence matched the sequence of the amplified cDNA fragment. The clone contains an open reading frame with one initiation codon but no termination codon at the 3'-end. In order to obtain the complete 3' end of the cDNA, another round of screening using the heart library was performed. Two clones were obtained, one which was identical to the previously identified incomplete clone and a second overlapping clone of about 1 kb that contained a translation termination codon. The Wnt-x human cDNA of about 1272 bp encodes a protein of about 397 amino acids. The encoded protein contains a putative signal peptide and is most similar to Wnt-2 with greater than 60% identity.

Expression Of Wnt Genes And Regulation By Vitamin D3

Northern analysis revealed that the expression of Wnt-x was detected in rat tibia and human giant cell tumor cells.

The expression level of Wnt-3 mRNA was detected as 4.0 and 1.8 Kb transcripts in mouse calvaria osteoblastic cells, and treatment with vitamin D3 (10 nM) or PTH (100 nM) increases its expression. Up-regulation of the expression of Wnt-3 with vitamin D3 was found only in MB 1.8 and MB 1.7 cells, which have inducing activity to generate osteoclast-like cells in an in vitro co-culture with bone marrow cells in the presence of vitamin D3. In contrast, no regulation with vitamin D3 was seen in MB 1.10 cells which have no inducing activity.

The expression of Wnt-5a was detected in mouse clonal calvarial cells, and its expression was down-regulated by treatment of vitamin D3 in co-culture with bone marrow cells and calvaria osteoblastic cells. No expression of Wnt-5a was found in heart, liver, spleen, intestine and muscle of rats. The transcripts of Wnt-6 were not detected in the cultured mouse calvaria cells. The expression of Wnt-6 mRNA was detected only in the rat preosteoblastic cell lines TRAB11 and RCT-1.

The following examples are provided for the purpose of illustrating the present invention without, however, limiting the same thereto.

EXAMPLE 1
Cells And Bone Tissues

Established mouse clonal osteoblastic cell lines from neonatal mouse calvaria were used in this study. MeB 1.7 and MB 1.8 have activity to induce osteoclast-like cells in co-culture with bone marrow cells in the presence of vitamin D3 in vitro. MB 1.10 passage 6 (P6) show osteoclast-inducing activity in vitro culture system, while passage 18 (18) has no inducing activity (10). Rat calvaria and tibia were removed rapidly after sacrifice from 3-day-old and 3-week-old normal rats (Taconic Farms, N.Y.), and frozen immediately in liquid nitrogen for RNA isolation. Human giant cell tumor (GCT) tissue was surgically removed from a 42-year-old female during surgery and provided by T. A. Einhorn, M. D. in Mount Sinai Medical Center in New York and frozen immediately for RNA preparation.

Cloning Of Wnt-x DNA

Preparation Of RNA And Northern Hybridization

Total RNAs were extracted by either a modified guanidinium hydrochloride method or a guanidinium isothiocyanate method (11, 12). Total RNA, ranging between about 20–30 µg, was separated on 0.9% agarose gels containing 6.6% formaldehyde and transferred to nylon filters (Hybond N, Amersham). After transfer and UV fixation (Autolinker, Strategene), the filters were hybridized with cDNA probes of PCR products in a solution containing 40–50% formamide (Hybrisol I and II, Oncor).

Polymerase Chain reaction (PCR)

Random primed cDNA libraries were prepared from total RNAs isolated from mouse calvaria cells, rat calvaria and human giant cell tumor cells, using the Moloney Murine Leukemia reverse transcriptase (M-MLVH-RT, BRL). Amplification cycles (denaturation at 94° C., 1 minute; annealing at 55° C., 2 minutes; extension at 72° C., 2 minutes; for 30 cycles) were carried out with Wnt primers-1, 2, 3 (0.5 UM each) with the Amplitaq kit and the DNA thermal cycler (Perkin Elmer Cetus). The PCR products were isolated from gel and cloned into pBS vector by blunt ligation. Clones were analyzed by digestion of miniprepa-ration of plasmid DNA with PvuII and by double-strand DNA sequencing (Sequenase, United States Biochemicals).

Wnt primer-1 (sense) GGG GAATTC CA(A/G) GA(A/G) TG(C/T) AA (A/G) TG(C/T)CAT (SEQ.ID.NO.: 1)

Wnt primer-2 (sense) GGG GAA TTC CAA GA(A/G)TG(C/T) AA(A/G)TG(C/T)CAC (SEQ.ID.NO.: 2)

Wnt primer-3 (antisense) AAA ATC TAG A(A/G)C A(A/G)C ACC A(A/G)TG(A/G)AA (SEQ.ID.NO.: 3)

Cloning Of Human Wnt-x cDNA

Random primed cDNA libraries were prepared from human giant cell tumor RNA. Amplification cycles were carried out with first Wnt primer pairs: Wnt primer 11 and 15 (0.5 µM each) in the same manner used above. Wnt primers 11 and 15 were designed according to the Wnt-x rat sequence and Wnt-x mouse consensus sequence, respectively. After completion of the first round of amplification, 5 µl of the reaction was used for a second cycle of amplification with a second set of primers: a partially nested oligomer Wnt primer 12 and the same 3' end primer Wnt-15 (0.5 µM each).

Wnt primer-11 (sense)—GGGAATTCCGGTGTGAGTGGCTCCT-GTAC (SEQ.ID.NO.: 4)

Wnt primer-12 (sense)—GGGAATTCCGGCTCCTGTACCCT-GCGCACCTG (SEQ.ID.NO.: 5)

Wnt primer-15 (antisense)—GGGAATTCCCGCAACACCAGTG-GAATTTGCACTCAC (SEQ.ID.NO.: 6)

Using primers designed according to the rat Wnt-x DNA sequence and mouse consensus sequence, PCR amplification of cDNA prepared from human giant cell tumor cells was carried out, and yielded a cDNA fragment of about 350 bp encoding the Wnt-x human gene. A cDNA fragment of the PCR product of human Wnt-x sequence was used as a probe to screen the human cDNA libraries. After screening approximately 0.5 million plaques of human heart library (Clontech, Calif.), we obtained only one clone of 1000 bp that matched the sequence of the PCR amplified fragment. Sequence analysis of the cloned cDNA revealed an open reading frame with an initiation codon at the 5' end and no termination codon. In order to obtain the complete 3' end coding region a second round of screening using the heart library was performed. Two clones were obtained, one which was identical to the previously identified incomplete clone and a second clone of about 1 kb that and contained a translation termination codon. The Wnt-x human cDNA is about 1272 bp (Table 1) and encodes a protein of about 397 amino acids (Table 2). The encoded protein contains a putative signal peptide and is most similar to Wnt-2 with about 66% identity.

TABLE 1

GAATTCCGGGGGCACCTTCCGGGCTGCGCGGCGGGAGTCTT
CGGGGAGCTATGCTGAGACCGGGTGGTGCGGAGGAAGCTGC
GCAGCTCCCGCTTCGGCGCGCCAGCGCCCCGGTCCCTGTGCC
GTCGCCCGCGGCCCCCGACGGCTCCCGGGCTTCGGCCCGCC
TAGGTCTTGCCTGCCTTCTGCTCCTGCTGCTGCTGACGCTGC
CGGCCCGCGTAGACACGTCCTGGTGGTACATTGGGGCACTG
GGGGCACGAGTGATCTGTGACAATATCCCTGGTTTGGTGAG
CCGGCAGCGGCAGCTGTGCCAGCGTTACCCAGACATCATGC
GTTCAGTGGGCGAGGGTGCCCGAGAATGGATCCGAGAGTGT
CAGCACCAATTCCGCCACCACCGCTGGAACTGTACCACCCT
GGACCGGGACCACACCGTCTTTGGCCGTGTCATGCTCAGAA
GTAGCCGAGACGGAGCTTTTGTATATGCCATCTCATCAGCA
GGGGTAGTCCACGCTATTACTCGCGCCTGTAGCCAGGGTGA

TABLE 1-continued

```
ACTGAGTGTGTGCAGCTGTGACCCCTACACCCGTGGCCGAC
ACCATGACCAGCGTGGGGACTTTGACTGGGGTGGCTGCAGT
GACAACATCCACTACGGTGTCCGTTTTGCCAAGGCCTTCGTG
GATGCCAAGGAGAAGAGGCTTAAGGATGCCCGGGCCCTCAT
GAACTTACATAATAACCGCTGTGGTCGCACGGTCAGTACTC
ATGTCTGTGCTGTGCGGCGGTTTCTGAAGCTGGAGTGTAAGT
GCCATGGCGTGAGTGGTTCCTGTACTCTGCGCACCTGCTGGC
GTGCACTCTCAGATTTCCGCCGCACAGGTGATTACCTGCGGC
GACGCTATGATGGGGCTGGTCAGGTGATGGCCACCCAAGAT
GGTGCCAACTTCACCGCAGCCCGCCAAGGCTATCGCCGTGC
CACCCGGACTGATCTTGTCTACTTGACAACCGCTCCAGATTA
CTGTGTCTTGGACAAGGCTGCAGGTTCCCTAGGCACTGCAG
GCCGTGTCTGCAGCAAGACATCAAAAGGAACAGACGGTTGT
GAAATCATGTGCTGTGGCCGAGGGTACGACACAACTCGAGT
CACCCGTGTTACCCAGTGTGAGTGCAAATTCCACTGGTGCTG
TGCTGTACGGTGCAAGGAATGCAGAAATACTGTGGACGTCC
ATACTTGCAAAGCCCCCAAGAAGGCAGAGTGGCTGGACCAG
ACCTGAACACACAGATACCTCACTCATCCCTCCC [SEQ ID NO:7].
```

TABLE 2

```
MLRPGGAEEAAQLPLRRASAPVPVPSPAAPDGSRASA
RLGLACLLLLLLLTLPARVDTSWWYIGALGARVICDN
IPGLVSRQRQLCQRYPDIMRSVGEGAREWIRECQHQF
RHHRWNCTTLDRDHTVFGRVMLRSSRDGAFVYAISS
AGVVHAITRACSQGELSVCSCDPYTRGRHHDQRGDF
DWGGCSDNIHYGVRFAKAFVDAKEKRLKDARALMN
LHNNRCGRTVSTHVCAVRRFLKLECKCHGVSGSCTL
RTCWRALSDFRRTGDYLRRRTDGAVQVMATQDGAN
FTAARQGYRRATRTDLVYLTTAPDYCVLDKAAGSLG
TAGRVCSKTSKGTDGCEIMCCGRGYDTTRVTRVTQC
ECKFHWCCAVRCKECRNTVDVHTCKAPKKAEWLDQ
T [SEQ.ID.NO.:8]
```

EXAMPLE 2
Cloning of the Wnt-x cDNA into *E. coli* Expression Vectors

Recombinant Wnt-x is produced in *E. coli* following the transfer of the Wnt-x expression cassette into *E. coli* expression vectors, including but not limited to, the pET series (Novagen). The pET vectors place Wnt-x expression under control of the tightly regulated bacteriophage T7 promoter. Following transfer of this construct into an *E. coli* host which contains a chromosomal copy of the T7 RNA polymerase gene driven by the inducible lac promoter, expression of Wnt-x is induced when an appropriate lac substrate (IPTG) is added to the culture. The levels of expressed Wnt-x are determined by the assays described above.

The cDNA encoding the entire open reading frame for Wnt-x is inserted into the NdeI site of pET 11a. Constructs in the positive orientation are identified by sequence analysis and used to transform the expression host strain BL21. Transformants are then used to inoculate cultures for the production of Wnt-x protein. Cultures may be grown in M9 or ZB media, whose formulation is known to those skilled in the art. After growth to an approximate $OD_{600}=1.5$, expression of Wnt-x is induced with 1 mM IPTG for 3 hours at 37° C. Authentic Wnt-x may be found in the insoluble inclusion body fraction from these cells. Soluble Wnt-x is extracted from the inclusion body fraction with 5M guanidine-HCl in a buffer containing 50 mM Tris-HCl (pH 8) and 100 mM dithiothreitol. Active Wnt-x is generated from this extract following dialysis against 100 volumes of 25 mM HEPES (pH 7.5), 5 mM dithiothreitol, 10% sucrose.

EXAMPLE 3
In Vitro Translation of Wnt-x mRNA and Xenopus Oocyte Expression

Wnt-x cDNA constructs are ligated into in vitro transcription vectors (the pGEM series, Promega) for the production of synthetic mRNAs.

Synthetic mRNA is produced in sufficient quantity in vitro by cloning double stranded DNA encoding Wnt-x mRNA into a plasmid vector containing a bacteriophage promoter, linearizing the plasmid vector containing the cloned Wnt-x-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded Wnt-x-encoding DNA is cloned into the bacteriophage promoter containing vector in the proper orientation using one or more of the available restriction endonuclease cloning sites on the vector which are convenient and appropriate for cloning Wnt-x DNA. The vector with the ligated Wnt-x DNA is used to transform bacteria, and clonal isolates are analyzed for the presence of the vector with the Wnt-x DNA in the proper orientation.

Once a vector containing the Wnt-x-encoding DNA in the proper orientation is identified and isolated, it is linearized by cleavage with a restriction endonuclease at a site downstream from, and without disrupting, the Wnt-x transcription unit. The linearized plasmid is isolated and purified, and used as a template for in vitro transcription of Wnt-x mRNA.

The template DNA is then mixed with bacteriophage-specific DNA-dependent RNA polymerase in a reaction mixture which allows transcription of the DNA template forming Wnt-x mRNA. Several bacteriophage-specific DNA-dependent RNA polymerases are available, including but not limited to T3, T7, and SP6 RNA polymerase. The synthetic Wnt-x mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5'terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified Wnt-x mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic Wnt-x mRNA to produce Wnt-x protein. The microinjected oocytes are incubated to allow translation of the Wnt-x mRNA, forming Wnt-x protein.

These synthetic mRNAs are injected into Xenopus oocytes (stage 5–6) by standard procedures [Gurdon, J. B. and Wickens, M. D. Methods in Enzymol. 101: 370–386, (1983)]. Oocytes are harvested and analyzed for Wnt-x expression as described below.

EXAMPLE 4
Cloning of Wnt-x cDNA into a Mammalian Expression Vector

Wnt-x cDNA expression cassettes are ligated at appropriate restriction endonuclease sites to the following vectors containing strong, universal mammalian promoters: pBC12BI [Cullen, B. R. Methods in Enzymol. 152: 684–704 1988], and pEE12 (CellTech EP 0 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci USA 80: 2495–2499 [1983]) driven by the SV40 early promoter. An SV40 polyadenylation sequence is generated by a PCR reaction defined by primers 13978-120 and 139778-121 using pD5 (Berker and Sharp, Nucl. Acid Res. 13: 841–857 [1985]) as template. The resulting 0.25 Kb PCR product is digested with ClaI and SpeI and ligated into the 6.7 Kb fragment of pEE 12 which had been likewise digested. The resultant plasmid is digested with BglII and SfiI to liberate the 3' portion of the SV40 early promoter and the GScDNA from the vector. A 0.73 Kb SfiI-XhoII fragment isolated from plasmid pFR400 (Simonsen, C. C. and Levinson, A. D. Proc. Natl. Acad. Sci USA 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the Wnt-x cDNA in the positive orientation with respect to the promoter are ligated into appropriate restriction sites 3' of the promoter and identified by restriction site mapping and/or sequencing. These cDNA expression vectors are introduced into various host cells including, but not limited to: [COS-7 (ATCC# CRL1651), CV-1 tat [Sackevitz et al., Science 238: 1575 (1987)], 293, L (ATCC# CRL6362)] by standard methods including but not limited to electroporation, or chemical procedures (cationic liposomes, DEAE dextran, calcium phosphate). Transfected cells and cell culture extracts can be harvested and analyzed for Wnt-x expression as described below.

All of the vectors used for mammalian transient expression can be used to establish stable cell lines expressing Wnt-x. Unaltered Wnt-x cDNA constructs cloned into expression vectors will be expected to program host cells to make intracellular Wnt-x protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing Wnt-x cDNA with a drug selection plasmid including, but not limited to G418, aminoglycoside phosphotransferase, pLNCX [Miller, A. D. and Rosman G. J. Biotech News 7: 980–990 (1989)]; hygromycin, hygromycin-B phosphotransferase, pLG90 [Gritz, L. and Davies, J., GENE 25: 179 (1983)]; APRT, xanthine-guanine phosphoribosyl-transferase, pMAM (Clontech) [Murray, et al., Gene 31: 233 (1984)] will allow for the selection of stably transfected clones. Levels of Wnt-x are quantitated by the assays described above.

Wnt-x cDNA constructs are ligated into vectors containing amplifiable drug-resistance markers for the production of mammalian cell clones synthesizing the highest possible levels of Wnt-x. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. USA 80: 2495 (1983)], transfected into DHFR-CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76: 3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 5

Cloning of Wnt-x cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing Wnt-x cDNA are produced by the following standard methods (In Vitrogen Maxbac Manual): the Wnt-x cDNA constructs are ligated downstream of the polyhedrin promoter in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of P-galactosidase expression (Vialard, et al. 1990, J. Virol., 64, pp 37–50). Following plaque purification and infection of sf9 cells with Wnt-x recombinant baculovirus, Wnt-x expression is measured by the assays described above.

The cDNA encoding the entire open reading frame for Wnt-x is inserted into the BamHI site of pBlueBacII. Constructs in the positive orientation with respect to the polyhedrin promoter are identified by sequence analysis and used to transfect Sf9 cells in the presence of linear AcNPV mild type DNA.

EXAMPLE 6

Cloning of Wnt-x cDNA into a yeast expression vector

Recombinant Wnt-x is produced in the yeast S. cerevisiae following the insertion of the optimal Wnt-x cDNA construct into expression vectors designed to direct the intracellular expression of heterologous proteins. For intracellular expression, vectors such as EmBLyex4 or the like are ligated to the Wnt-x cistron [Rinas, U. et al., Biotechnology 8: 543–545 (1990); Horowitz B. et al., J. Biol. Chem. 265: 4189–4192 (1989)]. The levels of expressed Wnt-x are determined by the assays described above.

EXAMPLE 7
Purification of Recombinant Wnt-x

Recombinantly produced Wnt-x may be purified by antibody affinity chromatography.

Wnt-x antibody affinity columns are made by adding the anti-Wnt-x antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents, if necessary such as detergents, and the cell culture supernatants or cell extracts containing Wnt-x or Wnt-x fragments are slowly passed through the column. The column is then washed with phosphate-buffered saline together with detergents, if necessary until the optical density (A280) falls to background, then the protein is eluted with 0.23M glycine-HCl (pH 2.6) together with detergents, if necessary. The purified Wnt-x protein is then dialyzed against phosphate buffered saline.

EXAMPLE 8
Procedure for identification of Wnt-x modulators

The expression vector produced in Example 4 is transferred into PC-1 2, C57MG, or RAC cells by standard methods known in the art [Maniatis et al., supra]. Cells which have taken up the vector are identified by their ability to grow in the presence of the selection agent or under selective conditions. Cells which are expressing the Wnt-x-encoding DNA produce RNA which is detected by Northern blot analysis as described in Example 1. Alternatively, cells expressing Wnt-x protein are identified by their secretion of Wnt-x protein into the culture medium, and the identification of the Wnt-x protein by Western blot analysis using the antibodies described above. Cells which express Wnt-x protein from the expression vector will display an altered morphology (oblong shaped cells) and/or enhanced growth properties.

Cells which express Wnt-x and display one or more of the altered properties described above are co-cultured with and without a putative modulator compound. The modulator compound will cause an increase or a decrease in the cellular response to Wnt-x expression, and will be either an activator or an inhibitor of Wnt-x activity, respectively.

Alternatively, recombinantly produced Wnt-x protein is added to cultures of PC-12, C57MG, or RAC cells and the cells display an altered morphology and/or display enhanced growth properties. A putative modulator compound is added to the cells with and without Wnt-x protein, and the cellular response is measured by direct observation of morphological characteristics of the cells and/or the cells are monitored for their growth properties. The modulator compound will cause an increase or a decrease in the cellular response to Wnt-x protein, and will be either an activator or an inhibitor of Wnt-x activity, respectively.

---

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGGGAATTCC ARGARTGYAA RTGYCAT 27

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGGGAATTCC AAGARTGYAA RTGYCAC 27

( 2 ) INFORMATION FOR SEQ ID NO:3:

( i ) SEQUENCE CHARACTERISTICS:
        ( A ) LENGTH: 25 base pairs

-continued ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:3:

AAAATCTAGA RCARCACCAR TGRAA          25

( 2 ) INFORMATION FOR SEQ ID NO:4:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:4:

GGGAATTCCG GTGTGAGTGG CTCCTGTAC          29

( 2 ) INFORMATION FOR SEQ ID NO:5:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:5:

GGGAATTCCG GCTCCTGTAC CCTGCGCACC TG          32

( 2 ) INFORMATION FOR SEQ ID NO:6:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

GGGAATTCCC GCAACACCAG TGGAATTTGC ACTCAC          36

( 2 ) INFORMATION FOR SEQ ID NO:7:

( i ) SEQUENCE CHARACTERISTICS:
            ( A ) LENGTH: 1272 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:7:

GAATTCCGGG GGCACCTTCC GGGCTGCGCG GCGGGAGTCT TCGGGGAGCT ATGCTGAGAC          60

CGGGTGGTGC GGAGGAAGCT GCGCAGCTCC CGCTTCGGCG CGCCAGCGCC CCGGTCCCTG          120

TGCCGTCGCC CGCGGCCCCC GACGGCTCCC GGGCTTCGGC CCGCCTAGGT CTTGCCTGCC          180

TTCTGCTCCT GCTGCTGCTG ACGCTGCCGG CCCGCGTAGA CACGTCCTGG TGGTACATTG          240

GGGCACTGGG GGCACGAGTG ATCTGTGACA ATATCCCTGG TTTGGTGAGC CGGCAGCGGC          300

AGCTGTGCCA GCGTTACCCA GACATCATGC GTTCAGTGGG CGAGGGTGCC CGAGAATGGA          360

-continued

| | | | | | |
|---|---|---|---|---|---|
| TCCGAGAGTG | TCAGCACCAA | TTCCGCCACC | ACCGCTGGAA | CTGTACCACC | CTGGACCGGG | 420 |
| ACCACACCGT | CTTTGGCCGT | GTCATGCTCA | GAAGTAGCCG | AGACGGAGCT | TTTGTATATG | 480 |
| CCATCTCATC | AGCAGGGGTA | GTCCACGCTA | TTACTCGCGC | CTGTAGCCAG | GGTGAACTGA | 540 |
| GTGTGTGCAG | CTGTGACCCC | TACACCCGTG | GCCGACACCA | TGACCAGCGT | GGGGACTTTG | 600 |
| ACTGGGGTGG | CTGCAGTGAC | AACATCCACT | ACGGTGTCCG | TTTTGCCAAG | GCCTTCGTGG | 660 |
| ATGCCAAGGA | GAAGAGGCTT | AAGGATGCCC | GGGCCCTCAT | GAACTTACAT | AATAACCGCT | 720 |
| GTGGTCGCAC | GGTCAGTACT | CATGTCTGTG | CTGTGCGGCG | GTTTCTGAAG | CTGGAGTGTA | 780 |
| AGTGCCATGG | CGTGAGTGGT | TCCTGTACTC | TGCGCACCTG | CTGGCGTGCA | CTCTCAGATT | 840 |
| TCCGCCGCAC | AGGTGATTAC | CTGCGGCGAC | GCTATGATGG | GGCTGGTCAG | GTGATGGCCA | 900 |
| CCCAAGATGG | TGCCAACTTC | ACCGCAGCCC | GCCAAGGCTA | TCGCCGTGCC | ACCCGGACTG | 960 |
| ATCTTGTCTA | CTTGACAACC | GCTCCAGATT | ACTGTGTCTT | GGACAAGGCT | GCAGGTTCCC | 1020 |
| TAGGCACTGC | AGGCCGTGTC | TGCAGCAAGA | CATCAAAAGG | AACAGACGGT | TGTGAAATCA | 1080 |
| TGTGCTGTGG | CCGAGGGTAC | GACACAACTC | GAGTCACCCG | TGTTACCCAG | TGTGAGTGCA | 1140 |
| AATTCCACTG | GTGCTGTGCT | GTACGGTGCA | AGGAATGCAG | AAATACTGTG | GACGTCCATA | 1200 |
| CTTGCAAAGC | CCCCAAGAAG | GCAGAGTGGC | TGGACCAGAC | CTGAACACAC | AGATACCTCA | 1260 |
| CTCATCCCTC | CC | | | | | 1272 |

( 2 ) INFORMATION FOR SEQ ID NO:8:

( i ) SEQUENCE CHARACTERISTICS:
( A ) LENGTH: 397 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

```
Met Leu Arg Pro Gly Gly Ala Glu Glu Ala Ala Gln Leu Pro Leu Arg
 1               5                  10                  15

Arg Ala Ser Ala Pro Val Pro Val Pro Ser Pro Ala Ala Pro Asp Gly
            20                  25                  30

Ser Arg Ala Ser Ala Arg Leu Gly Leu Ala Cys Leu Leu Leu Leu Leu
        35                  40                  45

Leu Leu Thr Leu Pro Ala Arg Val Asp Thr Ser Trp Trp Tyr Ile Gly
    50                  55                  60

Ala Leu Gly Ala Arg Val Ile Cys Asp Asn Ile Pro Gly Leu Val Ser
65                  70                  75                  80

Arg Gln Arg Gln Leu Cys Gln Arg Tyr Pro Asp Ile Met Arg Ser Val
                85                  90                  95

Gly Glu Gly Ala Arg Glu Trp Ile Arg Glu Cys Gln His Gln Phe Arg
            100                 105                 110

His His Arg Trp Asn Cys Thr Thr Leu Asp Arg Asp His Thr Val Phe
        115                 120                 125

Gly Arg Val Met Leu Arg Ser Ser Arg Asp Gly Ala Phe Val Tyr Ala
    130                 135                 140

Ile Ser Ser Ala Gly Val Val His Ala Ile Thr Arg Ala Cys Ser Gln
145                 150                 155                 160

Gly Glu Leu Ser Val Cys Ser Cys Asp Pro Tyr Thr Arg Gly Arg His
                165                 170                 175

His Asp Gln Arg Gly Asp Phe Asp Trp Gly Gly Cys Ser Asp Asn Ile
            180                 185                 190
```

-continued

| | | | | | | | | | | | | | | |
|---|---|---|---|---|---|---|---|---|---|---|---|---|---|---|
| His | Tyr | Gly 195 | Val | Arg | Phe | Ala | Lys 200 | Ala | Phe | Val | Asp | Ala 205 | Lys | Glu | Lys |
| Arg | Leu 210 | Lys | Asp | Ala | Arg | Ala 215 | Leu | Met | Asn | Leu | His 220 | Asn | Asn | Arg | Cys |
| Gly 225 | Arg | Thr | Val | Ser | Thr 230 | His | Val | Cys | Ala | Val | Arg 235 | Arg | Phe | Leu | Lys 240 |
| Leu | Glu | Cys | Lys | Cys 245 | His | Gly | Val | Ser | Gly 250 | Ser | Cys | Thr | Leu | Arg 255 | Thr |
| Cys | Trp | Arg | Ala 260 | Leu | Ser | Asp | Phe | Arg 265 | Arg | Thr | Gly | Asp | Tyr 270 | Leu | Arg |
| Arg | Arg | Thr 275 | Asp | Gly | Ala | Val | Gln 280 | Val | Met | Ala | Thr | Gln 285 | Asp | Gly | Ala |
| Asn | Phe 290 | Thr | Ala | Ala | Arg | Gln 295 | Gly | Tyr | Arg | Arg | Ala 300 | Thr | Arg | Thr | Asp |
| Leu 305 | Val | Tyr | Leu | Thr | Thr 310 | Ala | Pro | Asp | Tyr | Cys 315 | Val | Leu | Asp | Lys | Ala 320 |
| Ala | Gly | Ser | Leu | Gly 325 | Thr | Ala | Gly | Arg | Val 330 | Cys | Ser | Lys | Thr | Ser 335 | Lys |
| Gly | Thr | Asp | Gly 340 | Cys | Glu | Ile | Met | Cys 345 | Cys | Gly | Arg | Gly | Tyr 350 | Asp | Thr |
| Thr | Arg | Val 355 | Thr | Arg | Val | Thr | Gln 360 | Cys | Glu | Cys | Lys | Phe 365 | His | Trp | Cys |
| Cys | Ala 370 | Val | Arg | Cys | Lys | Glu 375 | Cys | Arg | Asn | Thr | Val 380 | Asp | Val | His | Thr |
| Cys 385 | Lys | Ala | Pro | Lys | Lys 390 | Ala | Glu | Trp | Leu | Asp 395 | Gln | Thr | | | |

What is claimed is:

1. An isolated and purified Wnt-x protein wherein said protein is characterized by the amino acid sequence:

MLRPGGAEEAAQLPLRRASAPVPVPSPAAPDGSRASA
RLGLACLLLLLLLLTLPARVDTSWWYIGALGARVICDN
IPGLVSRQRQLCQRYPDIMRSVGEGAREWIRECQHQF
RHHRWNCTILDRDHTVFGRVMLRSSRDGAFVYAISS
AGVVHAITRACSQGELSVCSCDPYTRGRHHDQRGDF
DWGGCSDNIHYGVRFAKAFVDAKEKRLKDARALMN
LHNNRCCGRTVSTHVCAVRRFLKLECKCHGVSGSCTL
RTCWRALSDFRRTGDYLRRRTDGAVQVMATQDGAN
FTAARQGYRRATRTDLVYLTTAPDYCVLDKAAGSLG
TAGRVCSKTSKGTDGCEIMCCGRGYDTTRVTRVTQC
ECKFHWCCAVRCKECRNTVDVHTCKAPKKAEWLDQ
T [SEQ.ID.NO.: 8]

2. An isolated and purified DNA molecule encoding a Wnt-x protein wherein said protein is characterized by the amino acid sequence as set forth in SEQ ID No:8.

3. An isolated and purified DNA molecule encoding a Wnt-x protein wherein said DNA molecule is characterized by the nucleotide sequence:

GAATTCCGGGGGCACCTTCCGGGCTGCGCGGCGGGAGTCTT
CGGGGAGCTATGCTGAGACCGGGTGGTGCGGAGGAAGCTGC
GCAGCTCCCGCTTCGGCGCGCCAGCGCCCCGGTCCCTGTGCC
GTCGCCCGCGGCCCCCGACGGCTCCCGGGCTTCGGCCCGCC
TAGGTCTTGCCTGCCTTCTGCTCCTGCTGCTGCTGACGCTGC
CGGCCCGCGTAGACACGTCCTGGTGGTACATTGGGGCACTG
GGGGCACGAGTGATCTGTGACAATATCCCTGGTTTGGTGAG
CCGGCAGCGGCAGCTGTGCCAGCGTTACCCAGACATCATGC
GTTCAGTGGGCGAGGGTGCCCGAGAATGGATCCGAGAGTGT
CAGCACCAATTCCGCCACCACCGCTGGAACTGTACCACCCT

-continued
GGACCGGGACCACACCGTCTTTGGCCGTGTCATGCTCAGAA
GTAGCCGAGACGGAGCTTTTGTATATGCCATCTCATCAGCA
GGGGTAGTCCACGCTATTACTCGCGCCTGTAGCCAGGGTGA
ACTGAGTGTGTGCAGCTGTGACCCCTACACCCGTGGCCGAC
ACCATGACCAGCGTGGGGACTTTGACTGGGGTGGCTGCAGT
GACAACATCCACTACGGTGTCCGTTTTGCCAAGGCCTTCGTG
GATGCCAAGGAGAAGAGGCTTAAGGATGCCCGGGCCCTCAT
GAACTTACATAATAACCGCTGTGGTCGCACGGTCAGTACTC
ATGTCTGTGCTGTGCGGCGGTTTCTGAAGCTGGAGTGTAAGT
GCCATGGCGTGAGTGGTTCCTGTACTCTGCGCACCTGCTGGC
GTGCACTCTCAGATTTCCGCCGCACAGGTGATTACCTGCGGC
GACGCTATGATGGGGCTGGTCAGGTGATGGCCACCCAAGAT
GGTGCCAACTTCACCGCAGCCCGCCAAGGCTATCGCCGTGC
CACCCGGACTGATCTTGTCTACTTGACAACCGCTCCAGATTA
CTGTGTCTTGGACAAGGCTGCAGGTTCCCTAGGCACTGCAG
GCCGTGTCTGCAGCAAGACATCAAAAGGAACAGACGGTTGT
GAAATCATGTGCTGTGGCCGAGGGTACGACACAACTCGAGT
CACCCGTGTTACCCAGTGTGAGTGCAAATTCCACTGGTGCTG
TGCTGTACGGTGCAAGGAATGCAGAAATACTGTGGACGTCC
ATACTTGCAAAGCCCCCAAGAAGGCAGAGTGGCTGGACCAG
ACCTGAACACACAGATACCTCACTCATCCCCTCCC [SEQ ID NO:7].

4. An expression vector for the expression of a Wnt-x protein in a recombinant host cell wherein said expression vector contains the DNA molecule of claim 3.

5. A host cell which expresses a recombinant Wnt-x protein wherein said host cell contains the expression vector of claim 4.

6. An antibody which specifically binds to a Wnt-x protein wherein said Wnt-x protein is characterized by the amino acid sequence of claim 1.

* * * * *